US011073512B2

(12) United States Patent
Coleman et al.

(10) Patent No.: US 11,073,512 B2
(45) Date of Patent: *Jul. 27, 2021

(54) MULTISIGNAL REAGENTS FOR LABELING ANALYTES

(71) Applicant: Enzo Life Sciences, Inc., Farmingdale, NY (US)

(72) Inventors: Jack Coleman, East Northport, NY (US); Maciej Szczepanik, Mount Sinai, NY (US); Richard Jin, Pennington, NJ (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 360 days.

This patent is subject to a terminal disclaimer.

(21) Appl. No.: 16/202,213

(22) Filed: Nov. 28, 2018

(65) Prior Publication Data

US 2019/0145964 A1  May 16, 2019

Related U.S. Application Data

(60) Continuation of application No. 15/609,360, filed on May 31, 2017, now Pat. No. 10,184,934, which is a division of application No. 13/556,425, filed on Jul. 24, 2012, now Pat. No. 9,696,298, which is a continuation-in-part of application No. 13/065,101, filed on Mar. 14, 2011, now Pat. No. 9,156,986, which is a continuation-in-part of application No. 12/399,393, filed on Mar. 6, 2009, now Pat. No. 8,394,949, which is a division of application No. 10/407,818, filed on Apr. 3, 2003, now Pat. No. 7,514,551.

(51) Int. Cl.

| | | |
|---|---|---|
| *G01N 33/53* | (2006.01) | |
| *C07H 21/00* | (2006.01) | |
| *C07H 21/04* | (2006.01) | |
| *C09B 11/08* | (2006.01) | |
| *C09B 11/24* | (2006.01) | |
| *C12Q 1/6818* | (2018.01) | |
| *G01N 33/58* | (2006.01) | |
| *G01N 33/82* | (2006.01) | |
| *G01N 33/94* | (2006.01) | |

(52) U.S. Cl.
CPC ............ *G01N 33/53* (2013.01); *C07H 21/00* (2013.01); *C07H 21/04* (2013.01); *C09B 11/08* (2013.01); *C09B 11/24* (2013.01); *C12Q 1/6818* (2013.01); *G01N 33/581* (2013.01); *G01N 33/82* (2013.01); *G01N 33/94* (2013.01)

(58) Field of Classification Search
CPC ...... G01N 33/53; G01N 33/581; G01N 33/82; G01N 33/94; C07H 21/00; C07H 21/04
See application file for complete search history.

(56) References Cited

U.S. PATENT DOCUMENTS

| | | |
|---|---|---|
| 4,081,525 A | 3/1978 | Knight et al. |
| 4,257,774 A | 3/1981 | Richardson et al. |
| 4,547,569 A | 10/1985 | Letsinger et al. |
| 4,585,862 A | 4/1986 | Wang et al. |
| 4,692,509 A | 9/1987 | Dattagupta et al. |
| 4,711,955 A | 12/1987 | Ward et al. |
| 4,876,187 A | 10/1989 | Duck et al. |
| 4,948,882 A | 8/1990 | Ruth et al. |
| 4,952,685 A | 8/1990 | Stavrianopoulos |
| 4,996,143 A | 2/1991 | Heller et al. |
| 5,013,831 A | 5/1991 | Stavrianopoulos |
| 5,175,270 A | 12/1992 | Nilsen et al. |
| 5,241,060 A | 8/1993 | Engelhardt et al. |
| 5,446,137 A | 8/1995 | Maag |
| 5,696,251 A | 12/1997 | Arnold et al. |
| 5,945,526 A | 8/1999 | Lee et al. |
| 6,008,373 A | 12/1999 | Waggoner et al. |

(Continued)

FOREIGN PATENT DOCUMENTS

| | | |
|---|---|---|
| EP | 0450594 | 10/1991 |
| EP | 0128332 | 8/1995 |

(Continued)

OTHER PUBLICATIONS

Bagalkot et al., "Quantum dot-aptamer conjugates for synchronous cancer imaging, therapy, and sensing of drug delivery based on bi-fluorescence resonance energy transfer," Nano Lett., vol. 7 pp. 3065-3070 (2007).

Halloran and Parker, "The preparation of nucleotide-protein conjugates: carbodimides as coupling agents," *J Immunol.*, vol. 96, p. 373 (1966).

Jablonski et al., "Preparation of oligodeoxynucleotide-alkaline phosphatase conjugates and their uses as hybridization probes," *Nucl. Acids. Res.*, vol. 14, pp. 6115-6128 (1986).

Kessler et al., "Methods for Nonradioactive Labeling of Nucleic Acids," *Nonisotopic Probing, Blotting and Sequencing*, 2$^{nd}$ edition, Larry J. Kricka (Ed.), Academic Press, Inc., San Diego, CA, pp. 42-109 (1995).

(Continued)

*Primary Examiner* — Jezia Riley
(74) *Attorney, Agent, or Firm* — Paul Diamond, Esq.

(57) ABSTRACT

Provided is a composition comprising an analyte bound covalently or through a first binding pair to a polymer. In this composition, the analyte is less than about 2000 MW; the polymer further comprises more than one signal or first member of a second binding pair; and the analyte is not a member of the first binding pair or the second binding pair. Also provided is an assay for an analyte. The assay comprises: combining a sample suspected of containing the analyte with the above-described composition and a binding agent that binds to the analyte; and detecting the signal or the first member of the second binding pair that is bound to the binding agent. Additionally provided is a multisignal labeling reagent comprising a first polymer covalently bound to (a) a reactive group or a first member of a first binding pair, and (b) more than one digoxigenin molecule.

6 Claims, 2 Drawing Sheets

Specification includes a Sequence Listing.

(56) References Cited

U.S. PATENT DOCUMENTS

| | | | |
|---|---|---|---|
| 6,046,038 | A | 4/2000 | Nilsen et al. |
| 6,110,687 | A * | 8/2000 | Nilsen .................. C07K 16/40 |
| | | | 435/6.19 |
| 7,125,660 | B2 | 10/2006 | Stanton |
| 7,166,478 | B2 | 1/2007 | Stavrianopoulos et al. |
| 7,425,436 | B2 | 9/2008 | Darzins |
| 7,429,472 | B2 | 9/2008 | Darzins |
| 7,432,105 | B2 | 10/2008 | Song et al. |
| 7,514,551 | B2 | 4/2009 | Rabbani et al. |
| 8,389,701 | B2 | 3/2013 | Rabbani et al. |
| 8,389,702 | B2 | 3/2013 | Rabbani et al. |
| 8,394,949 | B2 | 3/2013 | Rabbani et al. |
| 8,969,525 | B2 | 3/2015 | Mullenix et al. |
| 10,184,934 | B2 * | 1/2019 | Coleman ................. C09B 11/24 |
| 2003/0175828 | A1 | 9/2003 | Lazar |
| 2004/0161741 | A1 | 8/2004 | Rabbani et al. |
| 2004/0198971 | A1 | 10/2004 | Rabbani et al. |
| 2005/0137388 | A1 | 6/2005 | Rabbani et al. |
| 2005/0181383 | A1 * | 8/2005 | Su ....................... C12Q 1/6869 |
| | | | 435/6.18 |
| 2005/0272114 | A1 | 12/2005 | Darzins |
| 2006/0024738 | A1 | 2/2006 | Rabbani et al. |
| 2006/0024808 | A1 | 2/2006 | Darzins |
| 2008/0314766 | A1 | 12/2008 | Alocilja et al. |
| 2010/0273145 | A1 | 10/2010 | Pergolizzi et al. |
| 2011/0318788 | A1 | 12/2011 | Coleman et al. |
| 2012/0115169 | A1 | 5/2012 | Mullenix et al. |
| 2012/0219948 | A1 | 8/2012 | Yun et al. |
| 2013/0034866 | A1 | 2/2013 | Coleman et al. |
| 2016/0025716 | A1 | 1/2016 | Coleman et al. |

FOREIGN PATENT DOCUMENTS

| | | |
|---|---|---|
| EP | 0851228 | 7/1998 |
| EP | 1275737 | 1/2004 |
| EP | 1344835 | 3/2004 |
| WO | WO 2000/029624 | 5/2000 |
| WO | WO 2001/072766 | 10/2001 |
| WO | WO2008/024483 | 2/2008 |

OTHER PUBLICATIONS

Lee et al., "DNA sequencing with dye-labeled terminators and T7 DNA polymerase: effect of dyes and dNTPs on incorporation of dye-terminators and probability analysis of termination fragments," Nucl. Acids Res., vol. 20, pp. 2471-2488 (1992).

Loeschner and Engels, "The applications of universal DNA base analogues," Nucleosides Nucleotides, vol. 7, pp. 729 (1988).

Nielsen et al., "Sequence-selective recognition of DNA by strand displacement with a thymine-substituted polyamide," Sciences, vol. 254, p. 1497 (1991).

Ono et al., "2'-Fluoro modified nucleic acids: polymerase-directed synthesis, properties and stability to analysis by matrix-assisted laser desorption/ionization mass spectrometry," Nucleic Acids Research, vol. 25, No. 22, pp. 4581-4588 (1997).

Renberg, Bjorn, "Fluorescence-based ligand assays for protein detection using affibody affinity proteins," Department of Biotechnology, Royal Institute of Technology (KTH), Stockholm, Sweden, ISBN-91-7178-344-X.

Stec et al., "Automated solid-phase synthesis, separation, and stereochemistry of phosphorothioate analogs of oligodeoxyribonucleotides," J. Am. Chem. Soc., vol. 106, pp. 6077-6079 (1984).

Schwarz et al., Nature, vol. 314, pp. 111-114 (1995).

Walling et al., "quantum dots for Live Cell and In vivo Imaging," Int. J. Mol. Sci., vol. 10, pp. 441-491 (2009).

Zhang et al., "Tumor-Targeted Drug Delivery with Aptamers," Crr Med. Chem., vol. 18, No. 27, pp. 4185-4194 (2011).

Asseline et al., Oligodeoxynucleotides covalently linked to intercalating dyes as base sequence-specific ligands, influence of dye attachment site, EMBO , 1984, 795-800, 3.

Canellakis et al., Diacridines-double intercalators as chemotherapeutic agents, Biochemical Pharmacology, 1976, 231-236, 25.

Canellakis et al., Diacridines:bifunctional intercalators I. chemistry, physical chemistry and growth inhibitory properties, Biochimica et Biophysica Acta,1976, 277-289, 418.

Canellakis et al., Diacridines:bifunctional intercalators II. the biological effects of putrescine, spermidine and spermine diacridines on HeLa cells and on the L-1210 and P-388 leukemia cells, Biochimica et Biophysica Acta,1976, 290-299, 418.

Canellakis et al., Diacridines:bifunctional intercalators III. definition of the general site of action, Biochimica et Biophysica Acta,1976, 300-314, 418.

Capelle et al., Deoxyribonucleic acid bifunctional intercalators: kinetic investigation of the binding of several acridine dimers to deoxyribonucleic acid, Biochemistry, 1979, 3354-3362, 18.

Chen et al., Diacridines, bifunctional intercalators, chemistry and antitumor activity, Journal of Medicinal Chemistry, 1978, 868-874, 21.

Christy et al., DNA binding site of the growth factor-inducible protein Zif268, PNAS, 1989, 8737-8741, 86.

Elling et al., Conversion of antagonist-binding site to metal ion site in the tachykinin NK-1 receptor, Nature, 1995, 74-77, 374.

Fico et al., Bifunctional intercalators: relationship of antitumor activity of disacridines to the cell membrane, Science, 1977, 53-56, 198.

Gaugain et al., DNA bifunctional intercalators. 1. Synthesis and conformational properties of an ethidum homodimer and of an acridine ethidium heterdimer, Biochemistry, 1978, 5071-5077, 17.

Gaugain et al., DNA bifunctional intercalators. 2. Florescence properties and Dna binding interaction of an ethidium homodimer and an acridine ethidium heterodimer, Biochemistry, 1978, 5078-5088, 17.

Genest et al., Investigation of DNA dynamics and drug-DNA interaction by steady state fluorescence anistropy, Nucleic Acids Res., 1985, 2603-2615, 13.

Georghiou, S., Interaction of acridine drugs with DNA and nucleotides, Photochemistry and Photobiology, 1977, 59-68, 26.

Glover et al., Hairpin-shaped heterometallic luminescent lanthanide complexes for DNA intercalative recognition, J. Am. Chem, Soc., 2003, 9918-9919, 125.

HAMPSHIRE, A. and Fox, K., Preferred binding sites for the bifunctional intercalator TANDEM determined using DNA fragments that contain every symmetrical hexanucleotide sequence, Analytical Biochemistry, 2008, 298-303, 374.

Hannon, M., Supramolcular DNA recognition, Chemical Society Reviews, 2007, 280-295, 36.

King et al., Interactions of some novel amide-linked Bis(acridines) with deoxyribonucleic acid, Biochemistry, 1982, 4982-4989, 21.

Kobuta, Y. and Steiner, R., Fluorescence decay and quantum yield characteristics of acridine orange and proflavine bound to DNA, Biophysical Chemistry, 1977, 279-289, 6.

Loakes, D., The applications of universal DNA base analogues, Nucleic acids Res. 2001, 2437-2447, 29.

Mincheva et al., Chromosomal intergration sites of human papillimavirus dna in three cervical cancer cell lines mapped by in situ hybridization, Med Microbiol Immunol.,1987, 245-256, 176.

Maloney et al., Synthesis of acridine-based DNA bis-intercalating agents, Molecules, 2001, 230-243, 6.

Timtcheva et al., Homodimeric monomethine cyanine dyes as fluorescent proves of biopolymers, J. Photochemistry and Photobiology B: Biology, 2000, 130-135, 58.

Wakelin et al., Structural limitations on the bifunctional intercalation of diacridines in DNA, Biochemstry, 1978, 5057-5063, 17.

Wright et al., Effects of ring substituents and linker chains on the bifunctional intercalation of diacridines into deoxyribonucleic acid, Biochemistry, 1980, 5825-5836, 19.

Blomberg et al., Terbium and Rhodamine as Labels in a Homogeneous Time-resolved Fluorometric Energy Transfer Assay of the beta Subunit of Human Chorionic Gonadotropin in Serum, Clinical Chemistry 1999, 855-861, 45 (6).

Cayman Chemical Company, Cyclic AMP EIA Kit, caymanchem.com/pdfs/581001.pdf.

(56) References Cited

OTHER PUBLICATIONS

Chabardes et al., Adenylate Cyclase Responsiveness to Hormones in Various Portions of the Human Nephron, J. Clin. Invest. 1980, 439-448, 65.

Charlton and Porter, Isolation of Anti-Hapten Specific Antibody Fragments from Combinatorial Libraries, Methods in Molecular Biology 2002, 159-171, 178.

Enzo Life Sciences, Inc., cAMP Complete ELISA kit, static. enzolifesciences.com/fileadmin/files/manual/ADI-900-163_insert.pdf.

Grill and Cerasi, Stimulation by D-Glucose of Cyclic Adenosine 3′ : 5′-Monophosphate Accumulation and Insulin Release in Isolated Pancreatic Islets of the Rat, The Journal of Biological Chemistry 1974, 4196-4201, 249(13).

Haynes, Jr., Robert C., The Activation of Adrenal Phosphorylase by the Adrenocorticotropic Hormone, The Journal of Biological Chemistry 1958, 1220-1222, 233.

Lee et al., DNA sequencing with dye-labeled terminators and T7 DNA polymerase: effect of dyes and dNTPs on incorporation of dye-terminators and probability analysis of termination fragments, Nucleic Acids Research. 1992, 2471-2483, 20(10).

Lipkin et al., Adenosine-3′ : 5′-phosphoric Acid : A Proof of Structure, Journal of the American Chemical Society 1959, 6198-6203, 81.

Mayilo et al., Competitive homogeneous digoxigenin immunoassay based on fluorescence quenching by gold nanoparticles, Analytica Chimica Acta 2009,119-122, 646.

O'Beirne and Cooper, Heterogeneous enzyme immunoassay, The Journal of Histochemistry and Cytochemistry 1979, 1148-1162, 27(8).

Perkin Elmer, AlphaScreen CAMP Assay Kit, perkinelmer.com/Catalog/Product/ID/6760625D.

Promega, GloSensor CAMP Assay, promega.com/products/drug-discovery/gpcr-assays/glosensor-camp-assay/.

Szentivanyi, Andor, The beta adrenergic theory of the atopic abnormality in bronchial asthma, Journal of Allergy 1968, 203-232, 42.

Wang et al., Development of a Cyclic Adenosine Monophosphate Assay for Gi-Coupled G Protein-Coupled Receptors by Utilizing the Endogenous Calcitonin Activity in Chinese Hamster Ovary Cells, Assay and Drug Development Technologies 2011, 522-531, 9.

Winter et al., Making antibodies by phage display technology, Annu. Rev. Immunol. 1994, 433-455, 12.

Wong et al., Reproducibility and Correlations of Multiplex Cytokine Levels in Asymptomatic Persons, Cancer Epidemiol Biomarkers Prev 2008, 3450-3456, 17(12).

* cited by examiner

MULTISIGNAL REAGENTS FOR LABELING ANALYTES

CROSS-REFERENCE TO RELATED APPLICATIONS

This is a continuation of U.S. patent application Ser. No. 15/609,360 filed May 31, 2017, now U.S. Pat. No. 10,184,934, which is a division of U.S. patent application Ser. No. 13/556,425 filed Jul. 24, 2012, now U.S. Pat. No. 9,696,298, which is a continuation-in-part of U.S. patent application Ser. No. 13/065,101; filed Mar. 14, 2011, now U.S. Pat. No. 9,156,986, which is a continuation-in-part application of U.S. patent application Ser. No. 12/399,393; filed Mar. 6, 2009, now U.S. Pat. No. 8,394,949, which is a divisional of application Ser. No. 10/407,818 filed Apr. 3, 2003, now U.S. Pat. No. 7,514,551, the contents of each hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 27, 2018, is named ENZ-65-CIP2-D1-CON-103.txt and is 1.539 bytes in size.

BACKGROUND OF THE INVENTION

(1) Field of the Invention

The present application generally relates to assays for detecting analytes, e.g., proteins and small molecules (haptens). More specifically, this application provides reagents for improving the detection and quantitation of an analytes with assays that utilize an agent, such as an antibody, that binds to the hapten.

(2) Description of the Related Art

There is a high demand to determine the presence and concentration of analytes of interest, for example protein and small molecule ("hapten") analytes, which can be of environmental or medical concern. Examples of hapten analytes include fungal or microbial toxins as a threat to food safety, and drugs, steroids, hormones, proteins, peptides, lipids, sugars, receptors, nucleic acids, vitamins, etc., e.g., in mammalian fluid or tissue samples, to identify an intoxication, control the medication of therapeutic drugs with a narrow therapeutic window, etc.

Assays (e.g., immunoassays) utilizing an agent that binds to an analyte of interest (e.g., an antibody) have been developed for detecting numerous analyte compounds at very low levels. As is known in the art, antibodies that bind to small molecule analytes can be developed by, for example, using phage display techniques, or by utilizing an immunogen that comprises the analyte, or an analog of the analyte, covalently conjugated to a carrier protein or other immunogenic macromolecule. When using hapten immunogens, antibodies are generally elicited to the portion of the analyte that is distal to the chemical bond through which the hapten is conjugated to the carrier, such that the distal portion becomes an epitope of the carrier-hapten complex.

Immunoassays for analytes often take the form of competitive binding assays, where, for example, a labeled analyte competes with analytes in the sample for binding to antibodies fixed on a solid matrix. In those assays, the signal from the label decreases with increasing concentration of analyte in the sample. Examples of such an assay includes known assays for cAMP and vitamin D (see, e.g., Enzo Life Sciences, "cAMP Complete ELISA kit"; GE Life Sciences, "Cyclic-AMP Assay Kit"; Caymen Chemical Company, "Cyclic AMP EIA Kit"; PerkinElmer, "AlphaScreen® cAMP Assay Kit"; and Promega, "GloSensor™ cAMP Assay"). These competitive assays and similar assays are often improved by improving the signal intensity of the label.

The use of non-radioactive labels in biochemistry and molecular biology has grown exponentially in recent years. Among the various compounds used as non-radioactive labels, aromatic dyes that produce a fluorescent or luminescent signal are especially useful. Notable examples of such compounds include fluorescein, rhodamine, coumarin and cyanine dyes such as Cy3 and Cy5. Composite dyes have also been synthesized by fusing two different dyes together. See, e.g., Lee et al., 1992; and U.S. Pat. Nos. 5,945,526 and 6,008,373.

Non-radioactive labeling methods have been developed to attach signal-generating groups onto proteins, nucleic acids and haptens. This is generally achieved by modifying labels with chemical groups such that they would be capable of reacting with, e.g., the amine, thiol, and hydroxyl groups on proteins or haptens. Examples of reactive groups utilized for this purpose include activated esters such as N-hydroxysuccinimide esters, isothiocyanates and other compounds.

Labeled nucleotides are used for the synthesis of DNA and RNA probes in many enzymatic methods including terminal transferase labeling, nick translation, random priming, reverse transcription, RNA transcription and primer extension. Labeled phosphoramidite versions of these nucleotides have also been used with automated synthesizers to prepare labeled oligonucleotides. The resulting labeled probes are widely used in such standard procedures as northern blotting, Southern blotting, in situ hybridization, RNase protection assays, DNA sequencing reactions, DNA and RNA microarray analysis and chromosome painting.

There is an extensive literature on chemical modification of nucleic acids by means of which a signal moiety is directly or indirectly attached to a nucleic acid. See, e.g., U.S. Pat. Nos. 4,711,955 and 5,241,060, 4,952,685, 5,013,831, 7,166,478 and 7,514,551, and U.S. Patent Publication 2011/0318788.

The presence and nature of a linker arm may also improve the signaling characteristics of the labeled target molecule (see, e.g., U.S. Patent Publication 2011/0218788 and U.S. Pat. No. 7,514,551).

BRIEF SUMMARY OF THE INVENTION

The invention provided herein is based in part on the discovery that a multisignal labeling reagent, e.g., as described in U.S. Patent Publication 2011/0318788 and U.S. Pat. No. 7,514,551, can be advantageously utilized for labeling analytes, e.g., protein or on small molecule analytes, for example as a reagent in competitive immunoassays.

Thus, in some embodiments, a composition comprising an analyte bound covalently or through a first binding pair to a polymer is provided. In these embodiments, the analyte is less than about 2000 MW; the polymer further comprises more than one signal or first member of a second binding pair; and the analyte is not a member of the first binding pair or the second binding pair.

In other embodiments, an assay for an analyte is provided. The assay comprises: (a) combining a sample suspected of containing the analyte with a detection reagent and a binding agent that binds to the analyte, wherein the detection reagent comprises the analyte or an analyte analog bound covalently or through a first binding pair to a polymer, said polymer further comprising more than one signal or first member of a second binding pair, wherein the analyte or analyte analog is not a member of the first binding pair or the second binding pair; (b) removing any of the detection reagent that is not bound to the binding agent; and (c) detecting the signal or the first member of the second binding pair that is bound to the binding agent. In these embodiments, the amount of the signal or the first member of the second binding pair bound to the binding agent is inversely proportional to the analyte in the sample.

Additionally provided is a multisignal labeling reagent comprising a first polymer covalently bound to (a) a reactive group or a first member of a first binding pair, and (b) more than one digoxigenin molecule.

DETAILED DESCRIPTION OF THE INVENTION

Figure 1:
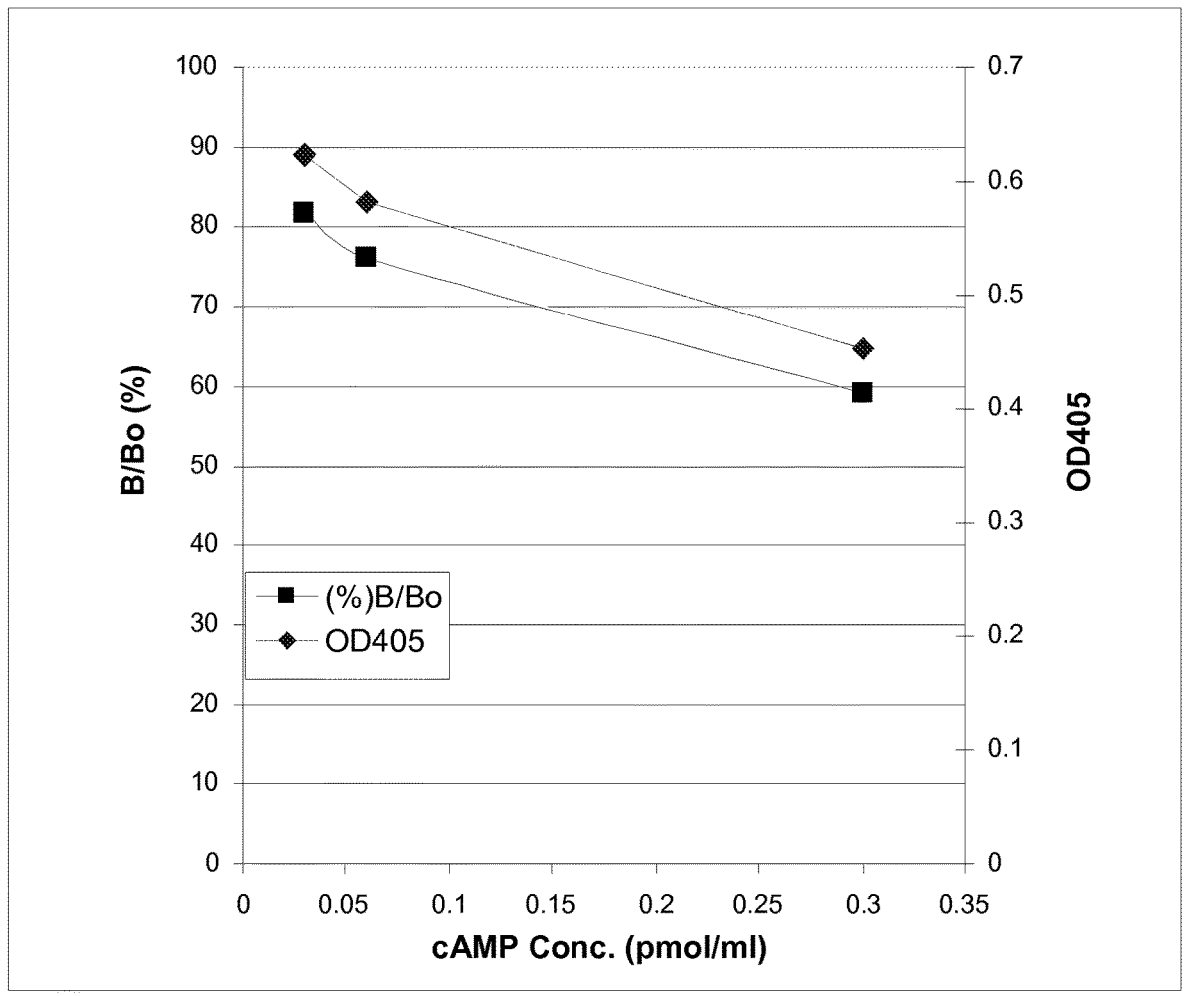
FIG. 1 is a graph showing the results of an immunoassay for cAMP utilizing a composition of the present invention.

As used herein, the singular forms "a", "an" and "the" are intended to include the plural forms as well, unless the context clearly indicates otherwise. Additionally, the use of "or" is intended to include "and/or", unless the context clearly indicates otherwise.

The present invention is based in part on the discovery that a multisignal labeling reagent, e.g., as described in U.S. Patent Publication 2011/0318788 and U.S. Pat. No. 7,514,551, can be advantageously utilized on small molecules, for example as a reagent in competitive immunoassays.

Thus, in some embodiments, a composition comprising an analyte bound covalently or through a first binding pair to a polymer is provided. In these embodiments, the analyte is less than about 2000 MW; the polymer further comprises more than one signal or first member of a second binding pair; and the analyte is not a member of the first binding pair or the second binding pair.

In various aspects of these embodiments, the analyte is less than about 1000 MW, less than about 500 MW, less than about 250 MW, less than about 200 MW, or less than about 150 MW.

As used herein, a polymer is an organic molecule comprising at least 3 repeating monomeric units such as amino acids, sugars, nucleotides or nucleotide analogs. The polymer of the composition can be comprised of any form of organic monomer and can be less than about 10 monomers, less than about 20 monomers, less than about 50 monomers, less than about 100 monomers, or about 100 or more monomers.

Non-limiting examples of polymers made from such monomeric units include nucleic acids, abasic nucleic acids, peptide nucleic acids, polypeptides, proteins, oligosaccharides, polysaccharides and organic polymers. The polymers used in the present invention may be isolated from biological sources or they may be created synthetically or in vitro. The polymers may also comprise multiples of only one particular type of monomeric unit, or they may comprise different types of monomeric units. For example, a chimeric oligomer or polymer can be a nucleic acid construct that comprises both a normal nucleic acid segment and a peptide nucleic acid segment, a combination of nucleotides and amino acids, or a combination of a segment of an abasic nucleic acid and a segment comprising a peptide nucleic acid.

Additionally, even when the monomeric units of the polymer are the same type of compound (e.g., all deoxyribonucleotides), they may be the same or they may be different. For instance, a nucleic acid polymer may be a homopolymer comprising a reiteration of a single base or it can be a heteropolymer having varied nucleotides. A polypeptide polymer may be homopolymeric and comprise multiples of a single amino acid or it may be heteropolymeric and comprise different amino acids. The labels in an oligomeric or polymeric labeling reagent may also be the same or they may be different. For instance, a labeling reagent that comprises two different dyes attached at discrete intervals on a polynucleotide may participate in energy transfer for signal generation.

The polymers in these compositions may comprise a single chain structure linking the monomeric units together or they may comprise more than one chain. For example, branched, double-stranded and triple-stranded nucleic acids may all find use with present invention. Additionally, the polymer comprising the signals or the first members of a second binding pair can be hybridized to the polymer that is bound to the analyte. Such multi-chain structures may provide useful properties. For example, a double-stranded nucleic acid is more rigid than a single stranded nucleic acid. The use of a double-stranded structure may allow better control over the distribution or spacing of labeled moieties where proximity or lack of proximity may be desirable. As is known, efficient signal generation by means of energy transfer depends upon a close proximity of donor and acceptor moieties and as such, establishment of a proximity between these moieties can be beneficial. Additionally, if a single dye species is being used as signal generators, a close proximity of some dye molecules can lead to a self-quenching phenomenon, and spreading out the locations of the dyes could thus be beneficial. The use of more than one chain may also convey other useful properties such as increasing the amount of signal generated or increasing the charge number. Multiple chains may also endow the system with flexibility of use. For example, a first nucleic acid strand may comprise a reactive group and a second nucleic acid strand with complementary sequences can comprise signal groups. By complementary base pairing between these strands, a complex can be formed that comprises a reactive group and signaling groups. See, e.g., FIG. 1 of U.S. Pat. No. 7,514,551. For example, they may comprise termini or extended chains with extended multiple charged groups. Other groups that may offer useful additional properties may also find use with the present invention.

In some embodiments, the polymer is an oligopeptide. The oligopeptide polymer can be more than about 100 amino acids or amino acid analogs, or less than about 100 amino acids or amino acid analogs, e.g., less than about 90, 80, 70, 60, 50, 40, 30, 20, 10 or 5 amino acids or amino acid analogs. In other embodiments, the polymer is a nucleic acid. Such a polymer can comprise any known nucleotide or nucleotide analog known in the art. The nucleic acid polymer can be more than about 100 nucleotides or nucleotide analogs, or less than about 100 nucleotides or nucleotides analogs, e.g., less than about 90, 80, 70, 60, 50, 40, 30, 25, 20, 15, 10 or 5 nucleotides or nucleotide analogs. The nucleic acid polymers can be synthesized by any means known in the art, for example as described in U.S. Patent Publication 2011/0318788 and U.S. Pat. No. 7,514,551.

In the invention compositions, the polymer can be bound to the analyte either covalently or through a first binding pair. Where the analyte is covalently bound to the polymer, the analyte and polymer can be joined by any method known in the art for the particular analyte and polymer. See, e.g., Example 1. As is known in the art, the analyte (or the polymer) can be modified to comprise a reactive group that reacts with a moiety on the polymer (or analyte). Where an immunoassay is already available for the analyte, the methods utilized to conjugate the analyte to the carrier protein to prepare the immunogen can generally also be utilized to conjugate the analyte to the polymer. Examples of reactive groups include but are not limited to active esters, groups capable of forming a carbon-carbon bonds and groups capable of forming bonds with O, N or S. Specific examples of such groups are isothiocyanate, isocyanate, monochlorotriazine, dichlorotriazine, mono- or di-halogen substituted pyridine, mono- or di-halogen substituted diazine, maleimide, aziridine, sulfonyl halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal, aldehyde, carbon-carbon double bonds, mercury salts, and any group capable of reacting with carbon-carbon double bonds, amines, hydroxyl groups, sulfhydryl groups and halogens.

Where the analyte is bound to the polymer through a first binding pair, the analyte is conjugated to one member of the first binding pair and the polymer is conjugated to the other member of the first binding pair. Non-limiting examples of binding pairs are a sugar-lectin, an antigen-antibody, a ligand-ligand receptor, a hormone-hormone receptor, an enzyme-substrate, a biotin-avidin, and a biotin-streptavidin. Methods for conjugating haptens and polymers to various members of binding pairs are well-known in the art. For the purposes of the invention compositions, a DNA supramolecular binding molecule or two DNA supramolecular binding molecules covalently joined by a linker group, as described in U.S. Patent Publication 2011/0318788, is considered a member of a binding pair, where the nucleic acid to which the DNA supramolecular binding molecule(s) bind is considered both the polymer and the other member of the binding pair.

As used herein, a "linker" or "linker arm" is a chemical moiety that separates one component of the composition (e.g., the polymer, hapten, binding pair member or signal) from another component. Thus, a linker may be used for example to separate the hapten from the first binding pair, the hapten from the polymer, the polymer from the first binding pair, the polymer from the second binding pair, the polymer from the signal, or the second binding pair from the signal.

A linker comprises a chain of atoms of any length that may be comprised of carbon, nitrogen, oxygen, sulfur in any combination and any other possible atom. The connecting chain can be saturated, unsaturated or can contain aromatic rings and the linking chain can be flexible or rigid. The connecting chain can further comprise any of the rigid units disclosed, e.g., in U.S. Patent Publication 2005/0137388.

The linker in these compounds can be rigid or flexible. Rigid linkers have been utilized with dimer intercalators. See, e.g., Glover et al. (2003). However, flexible linkers do not require the precise design required of rigid linkers, where the linker must precisely separate and orient the DNA supramolecular binding molecules to properly insert into the nucleic acid.

In some embodiments, the linker comprises an unsubstituted $C_1$-$C_{20}$ straight-chain, branched or cyclic alkyl, alkenyl or alkynyl group, a substituted $C_1$-$C_{10}$ straight-chain, branched or cyclic alkyl, alkenyl or alkynyl group wherein one or more C, CH or $CH_2$ groups are substituted with an O atom, N atom, S atom, NH group, CO group or OCO group, or an unsubstituted or substituted aromatic group. In more specific embodiments, the linker is —$(CH_2)$1-10-NH—$(CH_2)$1-10-. In still more specific embodiments, the linker is —$(CH_2)_{1-5}$—NH—$(CH_2)_{1-5}$—. One useful linker within these embodiments is —$(CH_2)_3$—NH—$(CH_2)_4$— (spermidine—see Examples 20-22 of U.S. Patent Publication 2011/0318788).

Linkers can be covalently attached to any of the substituents of the instant compositions by any means known in the art, e.g., through a reactive group as discussed above.

In some embodiments, the polymer is covalently bound to the signal moieties either directly or through a linker. Non-limiting examples of signals useful for these compositions are fluorescent dyes, colored dyes, radioactive molecules, chemiluminescent molecules and enzymes. Where the signal is an enzyme, the enzyme is capable of modifying a substrate to create a detectable signal. Non-limiting examples of such enzymes include alkaline phosphatase, horseradish peroxidase and luciferase.

In other embodiments, the polymer is covalently bound to more than one first member of a second binding pair, e.g., digoxigenin, fluorescein, biotin or dinitrophenol. In these embodiments, the first member of the second binding pair can be made into a detectable signal by adding a signal molecule that is bound to the second member of the second binding pair. Thus, a polymer bound to a hapten (e.g., cAMP—see Examples) that further comprises, e.g., more than one biotin moiety can be utilized in an assay where the biotin moieties are detected by adding streptavidin-alkaline phosphatase then an alkaline phosphatase substrate. See Example 3 below. In some of these embodiments, the composition further comprises more than one signal covalently bound to a second member of the second binding pair, wherein each signal-second member of the second binding pair is noncovalently bound to each first member of the second binding pair.

The compositions of these embodiments may also contain additional alkyl, aryl and/or polar or charged groups on any component of the composition, e.g., the hapten, the polymer, a binding pair member, a linker, or the signal. The polar or charged groups may include but are not limited to halogen, substituted or unsubstituted alkyl or aryl groups, saturated or unsaturated alkyl groups, alkoxy, phenoxy, amino, amido, and carboxyl groups, polar groups such as nitrates, sulfonates, sulfhydryl groups, nitrites, carboxylic acids, phosphates or any other such group or substituent.

The analytes for these compositions can be any hapten that can be manipulated as described above. Useful analytes include mammalian cellular metabolites, metabolites of microorganisms, medications, illicit drugs, vitamins, environmental pollutants, pesticides, and toxins. Specific non-limiting examples include cAMP, cGMP, 8-bromoadenosine 3',5'-cyclic monophosphate, cholesterol, a hydroxycholesterol, vitamin D, 25-hydroxy vitamin D, vitamin B12, vitamin E, vitamin B1, vitamin B6, ascorbic acid, retinol, biotin, folate, legumin, salbutamol, melamine, sulfaquinoxaline, an inositol phosphate, a phosphatidyl inositol phosphate, prednisone, pregnenolone, dexamethasone, triamcinolone, fludrocortisone, dihydrotachysterol, oxandrolone, testosterone, dihydrotestosterone, nandrolone, norethindrone, medroxyprogesterone acetate, progesterone, a glucocorticoid, aldosterone, estrogen, oxytocin, androstanediol glucuronide, bilirubin, warfarin, an estrogen, methotrexate, tobramycin, acetaminophen, encainide, fluoxetine, gentamycin, an aminoglycoside, amikacin, coenzyme Q10, theophylline, phenytoin, cimetidine, disulfiram, trazodone, ethanol, halothane, phenylbutazone, azapropazone, ibuprofen, amiodarone, imipramine, miconazole, metronidazole, nifedipine, chloramphenicol, trimethoprim, a sulfonamide, rifampin, cisplatin, vinblastine, bleomycin, oxacillin, nitrofurantoin, phenobarbital, primidone, carbamazepine, metoclopramide, cholestyramine, colestipol, neomycin, sulfasalazine, digoxin, indomethacin, diltiazem, erythromycin, tetracycline, itraconazole, nicardipine, triamterene, spironolactone, chlorpromazine, a cyclosporin, nortriptyline, ethosuximide, imipramine, codeine, lorazepam, topiramate, disopyramide, levetiracetam, clobazam, oxcarbazepine, fructosamine, caffeine, methaqualone, meprobamate, fluphenazine, a barbiturate, a phenothiazine, serotonin, valproic acid, digitoxin, maprotiline, lidocaine, mexiletine, primidone, risperidone, OH-rispiridone, a porphyrin, haloperidol, flecainide, tocainide, acetazolamide, a sulfonamide, verapamil, a metanephrine, an oxidized nucleotide, a mycotoxin, tetrahydrocannabinol, a cannabinoid, cocaine, LSD, an amphetamine, a barbiturate, heroin, methadone, nicotine, cotinine, a benzodiazepine, bis(2-ethylhexyl) phthalate, bisphenol A, hydralazine, atrazine, an organochloride insecticide, an organophosphate insecticide, or a carbamate insecticide. In some embodiments, the analyte is a steroid hormone, a glucocorticoid, oxytocin, cAMP, cGMP, hydroxycholesterol, vitamin D or 25-hydroxy vitamin D. In these compositions, the analyte could also be an analog of a compound of interest, e.g., any of the above compounds, particularly where the analog is able to compete with sample analyte for binding sites to a binding agent (e.g., an antibody), thus making the analog-polymer composition useful for competitive assays for the analyte (see further discussion below).

It is noted that certain analytes known to be members of a binding pair can also usefully be utilized as analytes in the invention compositions. An example is digoxigenin as an analyte, e.g., where the polymer is attached to the digoxigenin analyte through a biotin-streptavidin binding pair. In such a case, the digoxigenin is considered an analyte and not a member of a binding pair.

The above-described compositions, as well as multisignal labeling reagents bound to larger analytes such as proteins (for example as described in U.S. Patent Publication 2011/0318788 and U.S. Pat. No. 7,514,551) are particularly useful in assays for identification or quantitation of the analyte in a sample. The assays utilize a binding agent to the analyte, e.g., an antibody or analyte-binding fragment thereof.

Thus, an assay for an analyte is provided. The assay comprises: (a) combining a sample suspected of containing the analyte with a detection reagent and a binding agent that binds to the analyte, wherein the detection reagent comprises the analyte or an analyte analog bound covalently or through a first binding pair to a polymer, said polymer further comprising more than one signal or first member of a second binding pair, wherein the analyte or analyte analog is not a member of the first binding pair or the second binding pair; and (b) detecting the signal or the first member of the second binding pair that is bound to the binding agent. In these embodiments, the amount of the signal or the first member of the second binding pair bound to the binding agent is inversely proportional to the analyte in the sample.

The antibodies useful for these assays can be immunoglobulins of any vertebrate species, e.g., rabbit, goat, mouse, sheep, chicken, etc. and can be polyclonal or monoclonal. They can include the Fc region or they can be Fab or Fab2 fragments or otherwise engineered or manipulated to exclude all or part of the Fc region. Additionally, they can be from any source, e.g., from the serum of an animal injected with an immunogen such as any of the immunogens described above, or they can be from culture or ascites as is known in the art of hybridoma technology. Alternatively, they can be from recombinant sources, e.g., as described in Winter et al., 1994, or Charlton and Porter, 2002.

Any immunoassay known in the art as useful for analyte detection can be utilized for the instant assays. The relevant immunoassays generally utilize a competitive format, i.e., where the analyte in the sample competes with a labeled analyte or labeled hapten or hapten analog ("detection reagent") for anti-analyte antibody binding sites such that less detection reagent is bound when there is more hapten in the sample. Thus, in these competitive assays, an increasing amount of analyte in the sample results in less detection reagent bound to the solid phase, and consequently less signal. In various competitive assays, the sample can be added with the detection reagent to compete directly for antibody binding sites, or the sample and detection reagent can be added sequentially such that the detection reagent simply binds where the sample hapten is not bound.

The competitive assay for these embodiments can be homogeneous, where the signal detection step is performed without removing detection reagent that is not bound to the reagent. Nonlimiting examples include assays that utilize a change in FRET from a fluorescent signal when the detection reagent is bound to the binding agent. Alternatively, the assay can be heterogeneous, where detection reagent that is not bound to the binding agent is removed, so that the only signal is from bound detection reagent.

In some embodiments, the immunoassay is a direct competitive assay, utilized where the detection reagent comprises the analyte bound to the polymer comprising the signal, or an indirect competitive immunoassay, where the detection reagent comprises a first member of a second binding pair, e.g., a second antibody (for example an anti-digoxigenin antibody), biotin, or streptavidin. In the latter case, the amount of bound detection reagent is determined by adding the second member of the second binding pair that is bound to a signal (e.g., a digoxigenin-fluorescent dye complex, a biotin-alkaline phosphatase complex, a streptavidin-luciferase complex, etc.).

The immunoassays provided herein can take any format known in the art. In some embodiments, analyte antibodies are bound to the solid phase, either directly or indirectly, the latter being where the solid phase is coated with an anti-antibody (for example goat antibodies that bind to rabbit IgG antibodies [goat anti-rabbit IgG]) and the analyte antibodies are bound to the anti-antibody. The anti-antibodies are also known as "second antibodies." In these assays, the sample and detection reagent is added to the solid phase to compete with antibody binding sites on the coated solid phase. After washing, the signal is generated, which measures the amount of detection reagent that is bound to the solid phase. Numerous particular assays with this configuration can be devised without undue experimentation.

Numerous specific immunoassay formats are known that could be utilized with analyte-multisignal labeling reagents to determine an analyte in a sample. See, e.g., U.S. Patent Publication 2012/0115169, which provides a description of various relevant immunoassays. As described therein, the assay is performed in a liquid phase or on a solid phase, e.g., on a bead or a microplate, for example a 96 well microtiter plate. Nonlimiting examples of immunoassays useful in these methods are a radioimmunoassay, a Luminex® assay (see, e.g., Wong et al., 2008), a microarray assay, a fluorescence polarization immunoassay (see, e.g., U.S. Pat. No. 4,585,862), an immunoassay comprising a Förster resonance energy transfer (FRET) signaling system (see, e.g., Blomberg et al., 1999; Mayilo et al., 2009), a scintillation proximity assay, a fluorescence polarization assay, a homogeneous time-resolved fluorescence assay, an amplified luminescence assay ("ALPHAScreen"), an enzyme complementation assay, an electrochemiluminescence assay, and an enzyme immunoassay (a.k.a. enzyme linked immunosorbent assay [ELISA]). As is well known in the art, in ELISA, an enzyme combined with a substrate that becomes colored upon reaction with the enzyme provides the signal to quantify the antigen in the sample. See, e.g., O'Beirne and Cooper, 1979.

In various embodiments of these assays, the binding agent is an antibody or analyte-binding fragment thereof. In additional embodiments, the binding agent is bound to a solid phase.

In some embodiments, the analyte is less than about 2000 MW. In these embodiments, the detection reagent can be any of the analyte-polymer compositions described above. In some embodiments, the detection reagent comprises an analog to the analyte of interest bound to the polymer. Such a configuration may be favored to provide for more convenient production of the detection reagent, where the analyte analog provides for easier chemistry for conjugation to the polymer or first binding pair member. Utilization of an analyte analog in the detection reagent can also provide for more favorable conditions for binding to the binding agent, for example where a detection reagent with an analyte analog competes with sample analyte for antibody binding sites more favorably (e.g., providing better sensitivity or less background) than a detection reagent that utilizes the analyte.

In some aspects of these embodiments, the polymer comprises (a) more than one signal or (b) more than one first member of a second binding pair and a signal covalently bound to a second member of the second binding pair. In these aspects, each signal-second member of the second binding pair is noncovalently bound to each first member of the second binding pair. In alternative aspects, the signal covalently bound to a second member of the second binding pair is added after the combining step or the removing step.

With any of the assays described above, the signal can be any detectable label known in the art, for example a fluorescent dye, a colored dye, a radioactive molecule, a chemiluminescent molecule or an enzymes. Examples of useful enzymes in these embodiments are horseradish peroxidase, alkaline phosphatase and luciferase.

These assays can be used to detect any analyte that has a cognate binding agent or to which a binding agent (e.g., an antibody) can be synthesized. Useful analytes include mammalian cellular metabolites, metabolites of microorganisms, medications, illicit drugs, vitamins, environmental pollutants, pesticides, and toxins. Specific non-limiting examples include cAMP, cGMP, 8-bromoadenosine 3',5'-cyclic monophosphate, cholesterol, a hydroxycholesterol, vitamin D, 25-hydroxy vitamin D, vitamin B12, vitamin E, vitamin B1, vitamin B6, ascorbic acid, retinol, biotin, folate, legumin, salbutamol, melamine, sulfaquinoxaline, an inositol phosphate, a phosphatidyl inositol phosphate, prednisone, pregnenolone, dexamethasone, triamcinolone, fludrocortisone, dihydrotachysterol, oxandrolone, testosterone, dihydrotestosterone, nandrolone, norethindrone, medroxyprogesterone acetate, progesterone, a glucocorticoid, aldosterone, estrogen, oxytocin, androstanediol glucuronide, bilirubin, warfarin, an estrogen, methotrexate, tobramycin, acetaminophen, encainide, fluoxetine, gentamycin, an aminoglycoside, amikacin, coenzyme Q10, theophylline, phenytoin, cimetidine, disulfiram, trazodone, ethanol, halothane, phenylbutazone, azapropazone, ibuprofen, amiodarone, imipramine, miconazole, metronidazole, nifedipine, chloramphenicol, trimethoprim, a sulfonamide, rifampin, cisplatin, vinblastine, bleomycin, oxacillin, nitrofurantoin, phenobarbital, primidone, carbamazepine, metoclopramide, cholestyramine, colestipol, neomycin, sulfasalazine, digoxin, indomethacin, diltiazem, erythromycin, tetracycline, itraconazole, nicardipine, triamterene, spironolactone, chlorpromazine, a cyclosporin, nortriptyline, ethosuximide, imipramine, codeine, lorazepam, topiramate, disopyramide, levetiracetam, clobazam, oxcarbazepine, fructosamine, caffeine, methaqualone, meprobamate, fluphenazine, a barbiturate, a phenothiazine, serotonin, valproic acid, digitoxin, maprotiline, lidocaine, mexiletine, primidone, risperidone, OH-rispiridone, a porphyrin, haloperidol, flecainide, tocainide, acetazolamide, a sulfonamide, verapamil, a metanephrine, an oxidized nucleotide, a mycotoxin, tetrahydrocannabinol, a cannabinoid, cocaine, LSD, an amphetamine, a barbiturate, heroin, methadone, nicotine, cotinine, a benzodiazepine, bis(2-ethylhexyl) phthalate, bisphenol A, hydralazine, atrazine, an organochloride insecticide, an organophosphate insecticide, or a carbamate insecticide. In some embodiments, the analyte is a steroid hormone, a glucocorticoid, oxytocin, cAMP, cGMP, hydroxycholesterol, vitamin D or 25-hydroxy vitamin D.

The inventors have also discovered that multisignal labeling reagents, e.g., as described in U.S. Patent Publication 2011/0318788 and U.S. Pat. No. 7,514,551, are particularly effective when digoxigenin/anti-digoxigenin is used as a binding pair to join the polymer with the signal. See Examples 4-6.

Thus, in some embodiments, a multisignal labeling reagent is provided. The reagent comprises a first polymer covalently bound to (a) a reactive group or a first member of a first binding pair, and (b) more than one digoxigenin molecule. Here, polymers, reactive groups and binding pairs are as described above.

In various embodiments, the digoxigenin molecules on the polymer are used as a binding pair member for joining a signal molecule, where the other member of the binding pair is an anti-digoxigenin antibody that is further bound to at least one signal molecule. Signal molecules are described above, and could be, e.g., a fluorescent dye, a radioactive molecule or an enzyme. In various embodiments, each signal comprises an enzyme that is alkaline phosphatase, horseradish peroxidase or luciferase.

The multisignal labeling reagent of these embodiments can further comprise a linker moiety covalently linking (a) the first polymer to the reactive group or first member of the first binding pair and/or (b) the first polymer to the more than one digoxigenin molecules. Linker groups here are as described above.

In some embodiments, the first polymer is further bound to a second polymer, wherein the second polymer further comprises a signal molecule or a first member of a second binding pair. In most constructs, this configuration would cause a further amplification of the signal, e.g., for use where high sensitivity is desired. In some of these embodiments, the first polymer is covalently bound to the second polymer. Alternatively, the first polymer is bound to the second polymer through a third binding pair.

In various aspects of these multisignal labeling reagents, the reagent is bound to a target molecule through the reactive group or the first binding pair. The target molecule is not narrowly limited to any class of compound. Examples include haptens, proteins, oligopeptides, nucleic acids, nucleic acid analogs, oligosaccharides, polysaccharides, lipids and organic polymers.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1. Attaching an Oligonucleotide to cAMP (a) Synthesis of 2'-O-Succinyl-cAMP-NHS Ester 2'-O-succinyl-cAMP (3.0 mg, 6.9 μmol) was dissolved in 650 μl of anhydrous, amine-free DMSO and N-hydroxysuccinimide (11.5 mg, 100 μmol) was added. To the above clear solution, 1-ethyl-3-(3-dimethylaminopropyl) carbodiimide (EDCI) (13.4 mg, 70 μmol) dissolved in 150 μl of DMSO was added and the reaction mixture was incubated at room temperature overnight. The reaction progress was followed by TLC analysis (silica, isopropyl alcohol:$NH_4OH:H_2O$ 6:3:1). The crude product was used as DMSO solution in the following step (b).

(b) Addition of Oligo to 2'-O-Succinyl-cAMP-NHS Ester

To a solution of 5amCap 22-mer (20 nmole, 5'-amino-C6-TTG CTG AGG TCA TGG ATC GAG A-3') in Modification Buffer (100 mM sodium phosphate, 150 mM NaCl, pH 8.0), 45 molar equivalents of 2'-O-succinyl-cAMP-NHS ester in DMSO was added. The reaction mixture was incubated at room temperature for 18 h and after diluting with nuclease free water to decrease the amount of DMSO to 5% of the total, the mixture was purified on a 3 k Amicon diafiltration device. The cAMP-oligomer bioconjugate (~8 nmole) was identified and analyzed by HPLC analysis (Zorbax Oligo column, phosphate:acetonitrile gradient).

Example 2. Adding Poly Biotin to cAMP-Oligo

The cAMP-oligo described in Example 1 (0.6 nmole) was mixed with 0.9 nmole of Targext99

```
(5'-TAT ATT ATA TTA TAT TAT ATT ATA TTA TAT TAT
ATT ATA TTA TAT TAT ATT ATA TTA TAT TAT ATT ATA
TTA TAT TAT ATC TCG ATC CAT GAC CTC AGC-3').
```

The mixture contained 43 nmoles biotin-16-dUTP and 76 nmoles each of dATP, dCTP and dGTP in 10 mM Tris-HCl, pH 7.9, 10 mM $MgCl_2$, 1 mM DTT and 50 mM NaCl. T4 DNA polymerase exo minus (13 units) (Lucigen, Middleton, Wis.) was added, and the mixture was incubated at 37° C. for 90 min. The reaction was stopped with the addition of EDTA to a final concentration of 12.5 mM. The resulting poly-biotin cAMP was separated from free nucleotides using a NucAway (Ambion, Foster City, Calif.) size exclusion spin column equilibrated with phosphate buffered saline (PBS).

Example 3. Using cAMP Poly-Biotin to Quantify cAMP in a Sample cAMP poly-biotin was used instead of cAMP-alkaline phosphatase conjugate, to quantify low concentrations of cAMP in samples, in a competitive ELISA assay. Samples (100 μl), serial diluted standards, or a no cAMP control were added to microtiter wells coated with goat-anti-rabbit antibody (Enzo Life Sciences). 50 μl of cAMP poly-biotin (10 pmol/ml) were added to the wells followed by an addition of 50 μl antibody solution containing rabbit polyclonal antibody to cAMP (Enzo Life Sciences). Controls lacking rabbit anti-cAMP antibody were included. The plate was sealed and mixed briefly on a plate shaker (~500 rpm) for 5 s and incubated at 4° C. for greater than 12 hr. The contents of each well was emptied and washed three times, each with 400 μl wash buffer. After washing, 200 μl of streptavidin-alkaline phosphatase (2 ng/ml) (Thermo Scientific) was added to each well and incubated for 15 min on a plate shaker as above. The contents of the plate were emptied and wells washed 4 times with wash buffer as before. Alkaline Phosphatase Yellow (pNPP) Liquid Substrate (Sigma) (100 μl) was then added to each well and the plate incubated at room temperature for 1 hour without shaking. Stop solution consisting of 2 N NaOH (50 μl) was added to each well and the optical density of each well was read at 405 nm using a plate reader.

The sensitivity of the assay, defined as the concentration of cAMP measured at 2 standard deviations from the mean of 16 control wells without added cAMP was determined to be between 0.03-0.06 pmol/ml, a 5-10 fold increase over current assays using a cAMP-alkaline phosphatase conjugate. A sample result is shown in FIG. 1.

Example 4. Labeling a Biotinylated Oligonucleotide with Multiple Digoxigenin Molecules The oligonucleotide 5'-biotin-triethylene glycol (TEG)-TTGCTGAGGTCATGGATCGAGA-3' was extended with terminal deoxynucleotidyl transferase as follows. The oligonucleotide (160 pmoles) was mixed with 25 nmoles dATP, 5 (or 10) nmoles digoxigenin-labeled dUTP (Roche Diagnostics, Indianapolis, Ind.), 1 mM cobalt chloride, 1×TdT reaction buffer (ENZO Life Sciences, Farmingdale, N.Y.) and 40 units of terminal deoxynucleotidyl transferase in a total volume of 25 μl. This was incubated at 30° C. for 2 h. The reaction was stopped by the addition of EDTA to 12.75 mM. The extended oligo was purified using a Nucaway spin column (Ambion, Austin, Tex.), following the manufacturer's instructions. Oligo $dT_{21}$ (800 pmoles) was added to bind to the poly dA tracts created using terminal transferase. A complex of streptavidin with the biotinylated digoxigenin labeled oligonucleotide was created by mixing 150 pmoles of oligo with 136 pmoles streptavidin while vortexing.

Example 5. Labeling an Oligonucleotide Conjugated to Streptavidin with Multiple Digoxigenin Moieties The oligonucleotide 5'-aminoC6-TTGCTGAGGTCATG-GATCGAGA-3' was attached to streptavidin as described in Example 16 of U.S. Patent Publication 2011/0318788. The streptavidin oligonucleotide was extended with terminal transferase as follows. The streptavidin oligonucleotide (180 pmoles) was mixed with 25 nmoles dATP, 5 (or 10) nmoles digoxigenin labeled dUTP (Roche Diagnostics, Indianapolis, Ind.), 1 mM cobalt chloride, 1×TdT reaction buffer (ENZO Life Sciences, Farmingdale, N.Y.) and 40 units of terminal deoxynucleotidyl transferase in a total volume of 25 μl. This was incubated at 30° C. for a total of 2 hours. The reaction was stopped by the addition of EDTA to 12.75 mM. The extended oligo streptavidin was purified using a Nucaway spin column (Ambion, Austin, Tex.), following the manufacturer's instructions. 800 pmoles of oligo $dT_{21}$ was added to bind to the poly dA tracts created using terminal transferase.

Example 6. Labeling an Oligonucleotide Conjugated to Streptavidin Using DNA Polymerase and a Template The oligonucleotide 5'-aminoC6-TTGCTGAGGTCATG-GATCGAGA-3' was attached to streptavidin as described in Example 16 of U.S. Patent Publication 2011/0318788. The streptavidin oligonucleotide was extended using a template oligonucleotide as follows. A second oligo (5'-ACTTC-TACTT CTACTTCTAC TTCTACTTCT ACTTCTACTT CTACTTCTAC TCTTACTCTT ACTCTTCATT GGT-CATCTCG ATCCATGACC TCAGC-3') (MWG Operon, Huntsville, Ala.) was hybridized to the oligo streptavidin. The streptavidin oligo construct (113 pmoles) was incubated with 338 pmoles of template oligo in 50 mM NaCl, 10 mM Tris-HCl, 10 mM $MgCl_2$, 1 mM dithiothreitol, pH 7.9, 6.1 nMol S4FB-dUTP, 21 nMol each of dATP, dCTP and dGTP and 5.4 units of T4 DNA polymerase exo⁻ (Lucigen, Middleton, Wis.) in a total volume of 30 at 37° C. for 90 min. The extension reaction was stopped with 1 µl of 500 mM EDTA, and the unincorporated nucleotides are removed using NucAway spin columns (Applied Biosystems/Ambion, Austin, Tex.) as described by the manufacturer (http://www.ambion.com/techlib/spec/sp_10070.pdf).

Example 7. Binding and Detecting Poly-Digoxigenin Labeled Streptavidin

Figure 2:
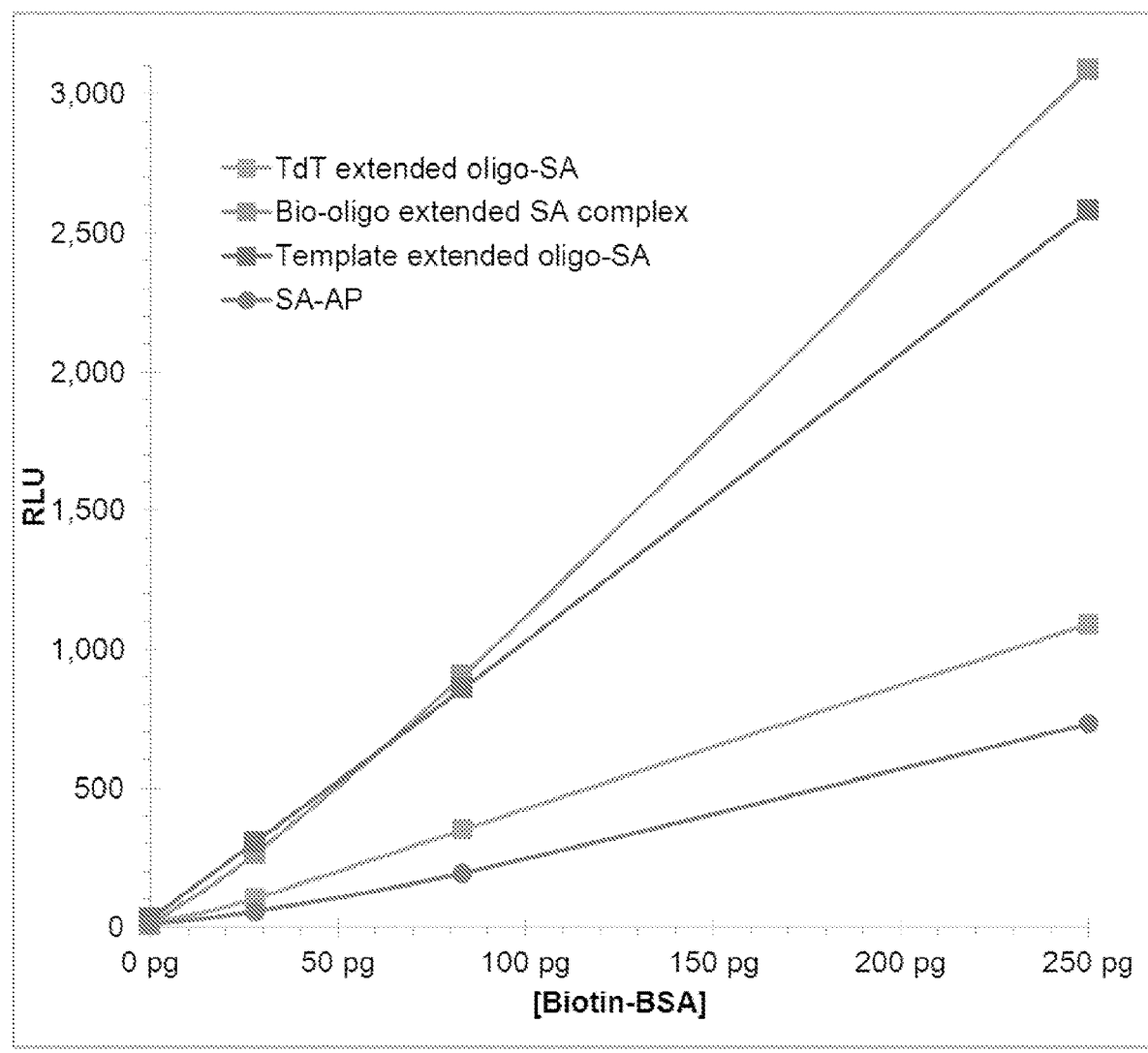
FIG. 2 is a graph showing the results of a comparison of four labeling reagents.

The streptavidin-poly-digoxigenin from Example 5 and a streptavidin-alkaline phosphatase complex were tested by binding to biotin attached to a 96-well microplate. Individual wells in the microplate were coated with varying concentrations of biotinylated-bovine serum albumin (BSA). Biotinylated BSA was produced by mixing 0.75 µmol BSA (fraction V, Sigma-Aldrich, St. Louis, Mo.) with 3.75 µmol ENZOTIN (NHS ester of biotin, ENZO Life Sciences, Farmingdale, N.Y.) in 50 mM sodium tetraborate, pH 8.5 at 22° C. for 4 hours. Unreacted biotin was removed using a Zeba spin column (Thermo-Pierce, Rockford, Ill.) as described by the manufacturer. The biotinylated-BSA (250 pg, 83.3 pg, 27.8 pg and 0 pg) was added to separate wells of black Maxisorb (Nunc, Roskilde, Denmark) 96-well microplate, diluted in PBS. After 12 hours at 4° C., the excess biotin BSA was washed out of the plate using 3 washes of 0.05% Tween20® in PBS for 5 minutes each. Blocking buffer (Thermo-Pierce, Rockford, Ill.) containing 0.05% Tween20® and 50 µg/ml single-stranded salmon sperm DNA was added to each well and the plate was incubated at 22° C. for 15 minutes with shaking. The blocking buffer was then removed, and the streptavidin-poly digoxigenin or commercial streptavidin alkaline phosphatase (Life Technologies, Carlsbad, Calif.) was then added to each well (100 µl, 4 nM) in the same blocking buffer and incubated with shaking for 60 minutes at 22° C. After 60 minutes, the streptavidin complexes were removed from the digoxigenin wells, and those wells were washed once with 200 µl PBS with 0.05% Tween20®. After removal of the wash, 100 µl of alkaline phosphatase labeled digoxigenin antibody (Roche, Indianapolis, Ind.) diluted 750 fold in blocking buffer was added to those wells. Incubation was continued at 22° C. for 60 minutes. All liquid was removed, and each well was washed 3 times with 0.05% Tween20® in PBS, for 5 min each. CDP-Star (Life Technologies, Carlsbad, Calif.) (100 µl) was added to each well, and the chemiluminescence produced was quantified using a BioTek SynergyMX (Winooski, Vt.) plate reader. The results are shown in FIG. 2.

All of the complexes with digoxigenin improved the signal compared to commercial alkaline phosphatase-labeled streptavidin. The oligonucleotide was more efficiently extended with terminal transferase if it was not attached to streptavidin first. Extension with T4 DNA polymerase on the streptavidin-oligonucleotide complex appears to be efficient.

REFERENCES

Blomberg et al., 1999, Clin. Chem. 45:855-61.
Caymen Chemical Company, "Cyclic AMP EIA Kit," at http://www.caymanchem.com/pdfs/581001.pdf.
Chabardes et al., 1980, J Clin Invest 65:439-448.
Charlton and Porter, 2002, Meth. Mol. Biol. 178:159-71.
Enzo Life Sciences, "cAMP Complete ELISA kit," at http://static.enzolifesciences.com/fileadmin/files/manual/ADI-900-163 insert.pdf).
GE Life Sciences, "Cyclic-AMP Assay Kit," at https://www.gelifesciences.com/gehcls_images/GELS/Related %20Content/Files/1314735988470/litdoccAMP_df_20110831002018.pdf.
Glover et al., 2003, J. Am. Chem. Soc. 125:9918-9919.
Grill and Cerasi, 1974, J Biol Chem 249:4196-4201.
Haynes, 1958, J Biol Chem 233:1220-1222.
Lee et al., (1992) Nucl. Acids Res. 20:2471-2488.
Lipkin et al., 1959, Journal of the American Chemical Society 81: 6198-6203.
Mayilo et al., 2009, Analytica Chimica Acta 646:119-22.
O'Beirne and Cooper, 1979, J. Histochem. Cytochem. 27:1148-62.
PerkinElmer, "AlphaScreeng_cAMP Assay Kit," at http://www.perkinelmer.com/Catalog/Product/ID/6760625D.
Promega, "GloSensor™ cAMP Assay," at http://www.promega.com/products/drug-discovery/gper-assays/glosensor-camp-assay/.
Szentivanyi, 1968, Journal of Allergy 42: 203-232.
Wang et al., 2011, Assay Drug Dev Technol 9: 522-531.
Winter et al., 1994, Ann. Rev. Immunol. 12:433-55.
Wong et al., 2008, Cancer Epidemiol. Biomarkers 17:3450-6.
U.S. Pat. No. 4,081,525.
U.S. Pat. No. 4,585,862.
U.S. Pat. No. 5,945,526.
U.S. Pat. No. 6,008,373.
U.S. Pat. No. 7,514,551.
U.S. Pat. No. 4,711,955.
U.S. Pat. No. 5,241,060.
U.S. Pat. No. 4,952,685.
U.S. Pat. No. 5,013,831.
U.S. Pat. No. 7,166,478.
U.S. Pat. No. 7,514,551.
U.S. Patent Publication 2005/0137388.
U.S. Patent Publication 2011/0318788.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A DNA oligonucleotide having a 5' end and a 3' end, comprising:
   a first member of a first binding pair attached at the 5' end of the DNA oligonucleotide, wherein the first binding pair is an antigen-antibody binding pair; and
   a first member of a second binding pair attached at the 3' end of the DNA oligonucleotide, wherein the second binding pair is an antigen-antibody binding pair.

2. The DNA oligonucleotide of claim 1, wherein the first member of the first binding pair is a protein.

3. The DNA oligonucleotide of claim 2, wherein the first member of the first binding pair is an antibody.

4. The DNA oligonucleotide of claim 1, wherein the first member of the second binding pair is a protein.

5. The DNA oligonucleotide of claim 4, wherein the first member of the second binding pair is an antibody.

6. The DNA oligonucleotide of claim 3, wherein the first member of the second binding pair is an antibody.

* * * * *

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttgctgaggt catggatcga ga                                              22

<210> SEQ ID NO 2
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tatattatat tatattatat tatattatat tatattatat tatattatat tatattatat    60
tatattatat tatattatat ctcgatccat gacctcagc                            99

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tttttttttt tttttttttt t                                               21

<210> SEQ ID NO 4
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acttctactt ctacttctac ttctacttct acttctactt ctacttctac tcttactctt    60
actcttcatt ggtcatctcg atccatgacc tcagc                                95